United States Patent
Akiyama et al.

(10) Patent No.: US 7,928,033 B2
(45) Date of Patent: Apr. 19, 2011

(54) CATALYST FOR REDUCING MERCURY, A MERCURY CONVERSION UNIT, AND AN APPARATUS FOR MEASURING TOTAL MERCURY IN COMBUSTION EXHAUST GAS BY USING THE SAME

(75) Inventors: Shigeyuki Akiyama, Kyoto (JP); Junji Kato, Kyoto (JP); Fujio Koga, Kyoto (JP); Koji Ishikawa, Kyoto (JP)

(73) Assignees: Horiba, Ltd., Kyoto (JP); Nippon Instruments Corporation, Tokyo (JP)

( * ) Notice: Subject to any disclaimer, the term of this patent is extended or adjusted under 35 U.S.C. 154(b) by 560 days.

(21) Appl. No.: 11/724,540

(22) Filed: Mar. 15, 2007

(65) Prior Publication Data
US 2007/0232488 A1    Oct. 4, 2007

(30) Foreign Application Priority Data
Mar. 31, 2006   (JP) ................... 2006-097630

(51) Int. Cl.
| | |
|---|---|
| *B01J 27/00* | (2006.01) |
| *B01J 27/02* | (2006.01) |
| *B01J 27/055* | (2006.01) |
| *B01J 21/18* | (2006.01) |
| *B01J 27/20* | (2006.01) |
| *B01J 20/00* | (2006.01) |
| *C01G 11/00* | (2006.01) |
| *C01G 9/00* | (2006.01) |
| *B01D 47/00* | (2006.01) |
| *B01D 53/46* | (2006.01) |
| *B01D 53/56* | (2006.01) |
| *B01D 53/02* | (2006.01) |
| *C01B 17/42* | (2006.01) |
| *C01B 31/24* | (2006.01) |
| *C01D 5/00* | (2006.01) |
| *C01D 15/06* | (2006.01) |
| *C01D 17/00* | (2006.01) |
| *C01D 7/00* | (2006.01) |
| *C01F 5/42* | (2006.01) |
| *C01F 11/46* | (2006.01) |
| *C01F 5/24* | (2006.01) |
| *A62D 3/30* | (2007.01) |
| *A62D 3/36* | (2007.01) |
| *A62D 3/40* | (2007.01) |

(52) U.S. Cl. ........ 502/208; 502/216; 502/218; 502/174; 502/400; 423/99; 423/107; 423/210; 423/519.2; 423/551; 423/554; 423/555; 423/419.1; 423/421; 423/430; 95/137; 95/900; 95/901; 588/313; 588/318; 588/321; 588/400; 588/410

(58) Field of Classification Search ................ 502/206, 502/216, 218, 174, 400, 208; 423/99, 107, 423/210, 519.2, 551, 554, 555, 419.1, 421, 423/430; 95/134, 900, 901; 588/313, 318, 588/321, 400, 410
See application file for complete search history.

(56) References Cited

U.S. PATENT DOCUMENTS
3,790,370 A * 2/1974 Lalancette .............. 210/721
(Continued)

FOREIGN PATENT DOCUMENTS
JP    61-050042    3/1986
(Continued)

OTHER PUBLICATIONS
"Mercury (II) removal from aqueous solutions and wastewaters using a novel cation exchanger derived from coconut coir pith and its recovery," T. S. Anirudhan et al. Journal of Hazardous Materials 157 (2008), pp. 620-627.*
(Continued)

Primary Examiner — Patricia L Hailey

(57) ABSTRACT

The present invention relates to a catalyst for reducing mercury, which comprises a reagent comprising any of the sulfites of potassium, sodium, calcium and magnesium, or any of the phosphates thereof, or a combination of them, as a main reagent of a catalyst component. And the present invention relates to the catalyst for reducing mercury, wherein the catalyst component is mixed with a different salt as an agent for inhibiting crystallization of the catalyst component.

20 Claims, 5 Drawing Sheets

U.S. PATENT DOCUMENTS

| | | | | |
|---|---|---|---|---|
| 3,847,598 | A | * | 11/1974 | Coulter et al. ............... 75/721 |
| 4,321,161 | A | * | 3/1982 | Watanabe et al. ............ 502/4 |
| 5,409,522 | A | * | 4/1995 | Durham et al. ............... 75/670 |
| 5,502,021 | A | * | 3/1996 | Schuster ........................ 502/400 |
| 5,607,496 | A | * | 3/1997 | Brooks ........................... 75/670 |
| 5,719,099 | A | * | 2/1998 | Bhat ............................... 502/414 |
| 5,879,948 | A | | 3/1999 | Van Pelt et al. |
| 6,126,910 | A | | 10/2000 | Wilhelm et al. |
| 6,271,173 | B1 | * | 8/2001 | Khare ............................. 502/406 |
| 6,388,165 | B1 | * | 5/2002 | Bhat ............................... 588/313 |
| 6,403,526 | B1 | | 6/2002 | Lussier et al. |
| 6,444,183 | B1 | * | 9/2002 | Mottot et al. ................. 423/210 |
| 6,620,236 | B2 | * | 9/2003 | Huntsman et al. ............ 106/713 |
| 6,818,043 | B1 | | 11/2004 | Chang et al. |
| 7,479,263 | B2 | * | 1/2009 | Chang et al. .................. 423/210 |
| 7,507,083 | B2 | * | 3/2009 | Comrie ............................ 431/2 |

FOREIGN PATENT DOCUMENTS

JP        2001-033434    *    2/2001

OTHER PUBLICATIONS

"Capture of mercury ions by natural and industrial materials," F. Di Natale et al. Journal of Hazardous Materials B132 (2006), pp. 220-225.*

"Advances in encapsulation technologies for the management of mercury-contaminated hazardous wastes," Paul Randall et al. Journal of Hazardous Materials B114 (2004), pp. 211-223.*

Methods for Determination of Mercury in Stack Gas; JIS Japanese Industrial Standars, JIS K 0222, 1997; Translated and Published by Japanese Standards Association; 19 pages.

* cited by examiner

CATALYST FOR REDUCING MERCURY, A MERCURY CONVERSION UNIT, AND AN APPARATUS FOR MEASURING TOTAL MERCURY IN COMBUSTION EXHAUST GAS BY USING THE SAME

BACKGROUND OF THE INVENTION

1. Field of the Invention

The present invention relates to a catalyst for reducing mercury, a mercury conversion unit and an apparatus for measuring total mercury in exhaust gas by using the same, and relates in particular to a catalyst for reducing mercury, a mercury conversion unit and an apparatus for measuring total mercury in exhaust gas by using the same, wherein total mercury in coal combustion exhaust gas for example is measured.

2. Description of the Related Art

As an apparatus for measuring total metal mercury in combustion exhaust gas, there has been conventionally used an apparatus for measuring total mercury for a fixed source by using a continuous measurement method or a dilution measurement method of using a gold amalgam catching/concentrating operation, stipulated under JIS K 0222. The dilution measurement method of using gold amalgam is a method of measuring metal mercury, which comprises heating a sample gas at high temperatures to reduce a mercury compound into metal mercury, then diluting it to catch mercury as gold amalgam, and after a predetermined time, re-gasifying amalgam mercury at high temperatures, and measuring metal mercury by a ultraviolet absorption method (see for example JIS K 0222-1997).

As applications are expanded in recent years, however, conventional methods of measuring mercury in, for example, exhaust gas from combustors are influenced by the presence of nitrogen oxides (NOx), sulfur dioxide ($SO_2$) or hydrogen chloride (HCl) in the exhaust gas, and thus it is difficult to obtain sufficiently accurate measurement values. At the request of improvement of measurement methods or of new measurement methods, the following various proposals are made at present.

Specifically, as shown in FIG. 7, there is proposed a method of continuously analyzing gaseous total mercury contained in exhaust gas upon treatment of sludge and wastes, wherein a mercury-containing gas is heated (about 230° C.) if necessary and then the mercury-containing gas is treated in a gaseous form with a heated (about 200° C.) solid reduction catalyst 21 consisting of a metal (metal tin, metal zinc etc.) thereby reducing a mercury compound (mercury chloride, mercury oxide etc.) in the mercury-containing gas into metal mercury which is then measured with a flameless atomic absorption spectrometer 22 (see, for example, JP-B 1-54655).

In an apparatus 31 for analyzing mercury in a mercuric chloride-containing gas, as shown in FIGS. 8(A) and (B), a reducing agent 34 comprising a stannous chloride coating 33 formed on the surface of tin particle 32 is charged into a reduction reactor 35, and by a reduction apparatus 36, the gas is passed through the reduction reactor 35, whereby $Hg^{2+}$ in mercuric chloride is reduced to $Hg^0$ by the reducing agent 34, and the reduced $Hg^0$ is analyzed by an analyzer (flameless atomic absorption spectrometer) 37. By doing so, mercury analysis can be properly carried out even if the concentration of mercuric chloride in the gas is low (see, for example, JP-A 2001-33434).

However, when the measurement methods or measuring apparatuses described above are used to measure total mercury in coal combustion exhaust gas, accurate measurement is difficult because of poisoning of the catalyst by metal oxides such as selenium oxide and arsenic oxide (both of which are gases) coexisting in exhaust gas and the influence of coexisting gas components $SO_2$, $NO_2$ and water on the catalytic activity.

That is, it was found through the inventors' verification that in a process of reduction treatment of mercury compounds (divalent mercury), metal oxides undergo reduction reaction simultaneously with the reaction of the mercury compounds, to easily form amalgam with mercury and catch mercury, thus gradually lowering measurement values and making mercury measurement infeasible in some cases. Particularly, coal combustion exhaust gas contains a relatively large amount of metal oxides such as those of lead (Pb) and selenium (Se) which easily form amalgam with mercury, and their influence cannot be negligible and their avoidance is difficult by the conventional methods.

The dilution measurement method of using a gold amalgam catching/concentrating operation prescribed in JIS K 0222 supra has problems such as significant errors in dilution, limitation to batch measurement, and deterioration in performance of high-temperature reduction catalyst. This conventional method makes use of a high-temperature catalyst, but there is also a problem of necessity for arrangement of an acid scrubber because $SO_2$ is oxidized at high temperatures to form $SO_3$ mist. Further, element mercury is easily oxidized again with gas-contacting materials (for example, stainless steel (SUS)) used for the high-temperature catalyst, so the selection of a material constituting the catalyst unit is necessary.

As described above, there are some demands for the apparatus for measuring total mercury, which is directed to coal combustion exhaust gas, but the apparatus for continuously measuring mercury by an extraction sampling system other than the dilution method of using a gold amalgam/concentrating operation is substantially not developed under the present circumstances.

In the atomic absorption spectrometry, photoabsorption in the ultraviolet range is utilized, and thus the interference influence of $SO_2$ and $NO_2$ coexistent at a high concentration of several thousand ppm in coal combustion exhaust gas cannot be negligible.

To cope with such demand, the object of the invention is to provide a catalyst for reducing mercury and a mercury conversion unit, which can maintain high reducing function even if various metal oxides and strongly acidic corrosive gases are coexistent such as in coal combustion exhaust gas. The present invention also provides an apparatus for measuring total mercury comprising the catalyst for reducing mercury and the mercury conversion unit, which is capable of continuous measurement with high accuracy and stability for a long time without undergoing the influence of coexisting components.

SUMMARY OF THE INVENTION

The present inventors made extensive study, and as a result they found that the above object can be achieved by a catalyst for reducing mercury, a mercury conversion unit and an apparatus for measuring total mercury in exhaust gas comprising the same, and the present invention was thereby completed.

The present invention relates to a catalyst for reducing mercury, which comprises a reagent comprising any of the sulfites of potassium, sodium, calcium and magnesium, or any of the phosphates thereof, or a combination of them, as a main reagent of a catalyst component.

As described above, when various metal oxides or strongly acidic corrosive gases such as in coal combustion exhaust gas are coexistent, continuous measurement with catalyst performance maintained without undergoing the influence of coexisting components is hardly feasible with the conventional apparatus for measuring total mercury. That is, the catalyst for reducing mercury is required to exhibit not only (A) selectivity reductive action for a mercury compound (bifunctional), but also (B) unreactivity with metal oxides, particularly a property of hardly forming amalgam with lead (Pb) and selenium (Se), and (C) corrosion resistance to strongly acidic gas. The present inventor examined various catalysts having a function of reducing mercury without undergoing such chemical influence, and as a result they found that a catalyst component comprising a reagent (reagent of the present invention) comprising any of the sulfites of potassium, sodium, calcium and magnesium, or any of the phosphates thereof, or a combination of them, as a main reagent of a catalyst component is very useful for function of reducing mercury.

That is, (A) with respect to the selectivity, a catalyst component comprising the reagent of the present invention as a main reagent reacts with a mercury compound (bifunctional) thereby exerting a reducing action selectively on the mercury compound. It was also found that the reagent of the present invention is poor in reactivity with acidic substances, thus eliminating the poisoning action, on the catalyst, of acidic substances such as $SO_2$ and $NO_2$ contained in a large amount in coal combustion exhaust gas. The present invention can secure a highly selective catalyst for reducing mercury by utilizing these findings.

Specific examples of the reductive reaction can include the reaction of mercury chloride ($HgCl_2$) with K or Na sulfite ($M_2SO_3$) as shown below. The details will be described later.

$$HgCl_2 + M_2SO_3 \rightarrow Hg + 2MCl + SO_2 + 1/2O_2 (300 \text{ to } 500° C.)$$

wherein M represents K or Na.

(B) Non-reactivity with the metal oxide is virtually not influenced in experiments. (C) The corrosion resistance is a property inherent in the reagent of the present invention and is not problematic in experiments. In the present invention, the properties of the reagent of the present invention described above (A)-(C) are utilized thereby providing a mercury reducing catalyst capable of maintaining high reducing performance.

The present invention relates to the catalyst for reducing mercury described above, wherein the catalyst component is mixed with a different salt as an agent for inhibiting crystallization of the catalyst component.

The reagent of the present invention comprises as a main reagent a water-soluble compound such as sulfite and phosphate, and therefore water if present can act as water of crystallization to cause crystallization of the catalyst component. When crystallization occurs, the resistance of a layer of the catalyst to gas passage is increased, and the efficiency of reduction may be reduced. Through inventor's verification, on one hand, it was found that when the reagent consists of one component or similar salts, crystallization of the reagent easily occurs, but the reagent when mixed with a different salt is hardly crystallized. According to the present invention based on this finding, the reagent of the present invention and a basic salt that is a different salt serving as a crystallization inhibitor are mixed with the catalyst component, whereby recrystallization at high temperatures is prevented and a large reaction surface area can be maintained. Thus, a mercury reduction catalyst capable of maintaining high reducing performance can be provided even for gas containing a large amount of water, such as coal combustion exhaust gas. As used herein, the "different salts" refer to salts different in crystalline structure. For example, inorganic sodium sulfite ($Na_2SO_3$) has a hexagonal system, and as the different salts correspond thereto, such as calcium carbonate ($CaCO_3$) has a trigonal or orthorhombic system, calcium sulfate ($CaSO_4$) has an orthorhombic system, and barium carbonate ($BaCO_3$) has a calcite structure.

The present invention relates to the catalyst for reducing mercury described above, wherein the catalyst component comprising the reagent as a main reagent is supported by a basic binder with an inorganic porous particle material as a carrier of the catalyst.

A major factor for determining catalyst activity includes properties of the reagent forming a catalyst, the surface area, etc. When exhaust gas such as coal combustion exhaust gas is a subject of measurement, the sample often contains a large amount of dust and mist, and how the effective surface area of the catalyst is secured is important for use of the mercury reduction catalyst for a long time. On the other hand, the reagent of the present invention is originally in a powdery form, and as a result of examination of how the reagent is converted into an easily handled catalyst with high efficiency, a mercury reduction catalyst securing the surface area of the catalyst, preventing abrasion of the catalyst and maintaining high reducing function for a long time could be provided by supporting the reagent by a basic binder with an inorganic porous particle material as a carrier of the catalyst.

The present invention relates to the catalyst for reducing mercury described above, wherein refractory and/or activated alumina is used as the inorganic porous particle material, and liquid glass and/or lithium silicate is used as the basic binder.

By the verification of the present invention described above, it was found that supporting the catalyst by the basic binder with an inorganic porous particle as a carrier of the catalyst is effective for securing the surface area of the catalyst, preventing abrasion of the catalyst and maintaining high reducing function of a long time. As a result of further examination of the inorganic porous particle material and the basic binder, it was found that the catalyst, wherein refractory and/or activated alumina is used as the inorganic porous particle material and liquid glass and/or lithium silicate is used as the basic binder, is formed into particles or in a honeycomb form, whereby the surface area of the catalyst can be secured, while abrasion of the catalyst is prevented, and its reducing function can be maintained for a long time.

The present invention relates to a mercury conversion unit comprising the above catalyst for reducing mercury charged into a predetermined container consisting of an inorganic material such as glass, quartz or ceramics or an oxidized metal such as oxidized stainless steel or titanium as a gas-contacting material wherein the operative temperature of the catalyst for reducing mercury is 300 to 500° C.

Generally, the reductive reaction is rendered more reactive as the temperature is increased, and the catalytic action is influenced significantly by the temperature, and thus a predetermined temperature is preferably maintained. As a result of verification, it was found that an operative temperature of 300° C. or more is preferable for securing and maintaining a predetermined efficiency of reduction with the reagent of the present invention as a catalyst for reducing mercury. Under a condition of further higher temperatures, on the other hand, there arise secondary problems such as formation of $SO_3$, so it was found that the upper limit of operative temperature is preferably about 500° C. It was found that as the gas-contacting material charged with the catalyst, materials such as SUS allow reduced mercury to be oxidized again, while inorganic materials such as glass, quartz and ceramics or metals such as oxidized SUS, titanium (Ti) etc. are preferable. According to the present invention, a mercury conversion unit wherein the operative temperature of the catalyst for reducing mercury is maintained in a predetermined range and the gas-contacting material is selected can be provided and applied to an apparatus for measuring total mercury in exhaust gas, which is capable of continuous measurement with high accuracy and stability for a long time without undergoing the influence of coexisting components.

The present invention relates to an apparatus for measuring total mercury using the above catalyst for reducing mercury or the above mercury conversion unit, which has the catalyst for reducing mercury or the mercury conversion unit in a part of a sample collection flow path, and after the treatment, a sample is introduced into an ultraviolet absorption analyzer.

As described above, the catalyst for reducing mercury or the mercury conversion unit according to the present invention has very excellent functions such as maintenance of high reducing function even in the coexistence of various metal oxides and strongly acidic corrosive gases. Accordingly, a very excellent apparatus for measuring total mercury can be constituted by applying such functions to the apparatus for measuring total mercury in exhaust gas, wherein the catalyst for reducing mercury or the mercury conversion unit is arranged in a part of a sample collection flow path, and a mercury compound in a sample is reduced and converted into element mercury which is then measured by an ultraviolet absorption analyzer. Particularly by using an ultraviolet absorption analyzer having selectivity for element mercury, an apparatus for measuring total mercury in exhaust gas, which is capable of continuous measurement with high accuracy and stability for a long time without being influenced by coexisting components, can be provided.

The present invention relates to the apparatus for measuring total mercury in exhaust gas, wherein a mist capturing agent or a counteragent is used in a pre-stage for the catalyst for reducing mercury or the mercury conversion unit in the sample collection flow path.

As described above, the catalyst for reducing mercury or the mercury conversion unit according to the present invention is used by limiting the operative temperature (500° C. or less) such that the reducing function is maintained for a long time. However, when a sample itself contains a substance such as $SO_3$ mist or oil mist causing corrosion of the sample collection flow path or poisoning the catalyst, limitation of the operative temperature cannot be said to be satisfactory. In such case, the present invention makes use of a mist capturing agent or a counteragent in a pre-stage for the catalyst for reducing mercury or the mercury conversion unit in the sample collection flow path, whereby the functions of the catalyst for reducing mercury or the mercury conversion unit can be maintained for a long time to enable continuous measurement with high accuracy and stability for a long time.

According to the present invention, there can be provided a catalyst for reducing mercury and a mercury conversion unit capable of maintaining high reducing function even in the coexistence of various metal oxides and strongly acidic corrosive gases such as coal combustion exhaust gas, which has conventionally been difficult as described above. There can also be provided an apparatus for measuring total mercury in exhaust gas, which is capable of continuous measurement with high accuracy and stability for a long time without being influenced by coexisting components.

Figure 1:
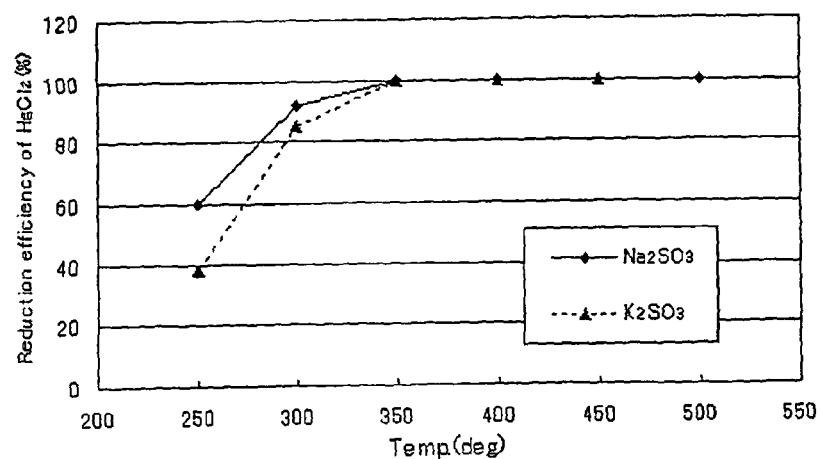
FIG. 1 is an illustration showing temperature characteristics for efficiency of reduction with the reagent of the present invention.

In the drawings, 1 is a mercury conversion unit; 2, a container; 3, a catalyst for reducing mercury; 4, a heating means; 10, an ultraviolet absorption analyzer; 11, a purification apparatus; and 18, a scrubber unit.

DETAILED DESCRIPTION OF THE INVENTION

Hereinafter, embodiments of the present invention are described in more detail by reference to the Drawings.

<Fundamental Constitution of the Mercury Reduction Catalyst According to the Present Invention>

The fundamental constitution of the mercury reduction catalyst according to the present invention is that the reagent of the present invention (corresponding to "a reagent comprising any of the sulfites of potassium, sodium, calcium and magnesium, or any of the phosphates thereof, or a combination of them") is contained as a main reagent of the catalyst component. That is, the reagent of the present invention exerts reducing action selectively on a mercury compound (bifunctional) to covert it into element mercury, by utilizing the unique characteristics: (A) selectivity of reducing catalyst action for a mercury compound (bifunctional) and (B) unreactivity with coexisting acidic substances. The reagent of the present invention is poor in (C) reactivity with acidic substance such as $SO_2$ and $NO_2$, to eliminate the poisoning action thereof on the catalyst (poisoning eliminating function). The catalyst for reducing mercury according to the present invention refers broadly to a mercury reduction catalyst comprising the reagent of the invention as a main reagent to which a substance functioning as a co-catalyst and an agent for inhibiting crystallization of the catalyst component are added to improve characteristics of the catalyst for reducing mercury.

Hereinafter, what is verified for (A) selectivity of reducing catalysis action, (B) unreactivity with metal oxides and (C) poisoning elimination function, which are required of the catalyst for reducing mercury, is described on the basis of the functions of the reagent of the present invention.

(A) Reducing Catalyst Function of the Reagent of the Present Invention

For the reducing catalyst function of the reagent of the present invention, the selectivity of reduction action for a mercury compound (bifunctional) is required. Now, the reduction of $HgCl_2$ as a major component in coal combustion exhaust gas by the catalyst action is described.

(A-1) Principle of Operation of Reductive Catalyst Reaction

It is considered that in a solid-gas reaction system, reductive reaction of mercury proceeds to such a state that a more sable compound is formed. That is, in the reaction of $HgCl_2$, except for high-temperature conditions of 600° C. or more, the degree of reactivity of the reagent of the present invention with the mercury compound (bifunctional) involves in the reactivity of the cation constituting the reagent of the present invention with chlorine (Cl) constituting $HgCl_2$ and the reactivity of the anion constituting the reagent of the present invention with Hg. Accordingly, the progress of the reaction can be judged by comparing the estimated formation system with the energy of formation of the substance to be formed ($\Delta H$, kJ/mol) and by analyzing the degree of the energy of formation of the acting substance.

(A-2) Type of the Reagent of the Present Invention

As a result of verification based on the analysis described above, it was found that the reagent of the present invention serving as a main reagent of the catalyst component is preferably a heat-resistant reagent, and the cation is preferably a salt of an alkali metal such as potassium (K) or sodium (Na) or an alkaline earth metal such as calcium (Ca) or magnesium (Mg). It was found that the anion is particularly preferably sulfites or phosphates. Specific reagents composed of such combinations are shown in Table 1.

TABLE 1

| | Reagent |
|---|---|
| Sulfites | Potassium Sulfite($K_2SO_3$) |
| | Sodium Sulfite($Na_2SO_3$) |
| | Calcium Sulfite($CaSO_3$) |
| | Magnesium Sulfite($MgSO_3$) |
| Phosphates | Potassium Phosphate($K_3PO_4$) |
| | Sodium Phosphate($Na_3PO_4$) |
| | Calcium Phosphate($Ca_3(PO_4)_2$) |
| | Magnesium Phosphate($Mg_3(PO_4)_2$) |

(A-3) Evaluation Test

With respect to the salts mentioned as the reagent of the present invention, the analysis in (A-1) was validated in a verification test to give the following new findings:

(a) Test Method (a-1) At a temperature of 300 to 500° C., a standard solution of mercuric chloride ($HgCl_2$) is gasified and passed through the catalyst column to determine the recovery of Hg.

(a-2) In the reagent of the present invention, special-grade reagents were used, and for the reagent of the present invention in a powdery form, refractory porous particles were used after dilution to about 30% (wt/wt). $Na_2SO_3$ was used by adhering it to the porous particle substance.

(a-3) Since $SO_2$ is contained at high concentration in exhaust gas, the reactivity of the reagent of the present invention with $SO_2$ or the stability of the reaction product can influence the reactivity of the reagent of the present invention with $HgCl_2$, thereby influencing the efficiency of reduction with the reagent of the present invention. This was verified by the method (a-1) at a reaction temperature of 400° C. in the coexistence of $SO_2$.

(b) Test Results (b-1) With Respect to Sulfites

Effective efficiency of reduction could be achieved by various sulfites such as alkali metal salts $Na_2SO_3$ and $K_2SO_3$ and alkaline earth metal salts $CaSO_3$ and $MgSO_3$. Specifically, 95% or more efficiency of reduction was confirmed by every sulfite at 400° C. at SV=1000 $hr^{-1}$. The same results could also be obtained by using a mixture thereof.

(b-2) With Respect to Phosphates

As effective compounds other than the sulfites, phosphates $Na_3PO_4$ and $K_3PO_4$ and $Ca_3(PO_4)_2$ and $Mg_3(PO_4)_2$ were revealed to exhibit 95% or more efficiency of reduction of $HgCl_2$ in the same temperature range.

(b-3) With Respect to Other Salts Stable at High Temperatures

It was found that salts stable at high temperatures such as sodium sulfate ($Na_2SO_4$), NaCl, KCl, calcium chloride ($CaCl_2$), barium chloride ($BaCl_2$) do not react at all.

(b-4) With Respect to Reductive Reaction in the Coexistence of $SO_2$

It was found that in the coexistence of $SO_2$ at a reaction temperature of 400° C., $Na_2SO_3$, $K_2SO_3$, $CaSO_3$ and $MgSO_3$ contribute to the reductive reaction of $HgCl_2$.

(A-4) Mechanism of Reductive Reaction (a) On the basis of the findings described above, the mechanism of the reductive reaction is organized below. The salts were classified into 2 groups: (a-1,2) alkali meal (M: for example, Na, K) sulfite ($M_2SO_3$) and phosphate ($M_3PO_4$) and (a-3,4) alkaline earth metal (M': for example, Ca, Mg) sulfite ($M'SO_3$) and phosphate ($M'_3(PO_4)_2$). The reaction temperature was 400° C.

(a-1) Reaction Formula:

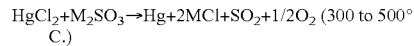

$$HgCl_2+M_2SO_3 \rightarrow Hg+2MCl+SO_2+1/2O_2 \text{ (300 to 500° C.)}$$

wherein M represents K or Na. For example, more stable potassium chloride (KCl) is formed by reaction with potassium sulfite ($K_2SO_3$), and sodium chloride (NaCl) is formed by reaction with sodium sulfite ($Na_2SO_3$).

(a-2) Reaction Formula:

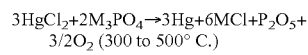

$$3HgCl_2+2M_3PO_4 \rightarrow 3Hg+6MCl+P_2O_5+3/2O_2 \text{ (300 to 500° C.)}$$

wherein M represents K or Na. For example, more stable potassium chloride (KCl) is formed by reaction with potassium phosphate ($K_3PO_4$), and sodium chloride (NaCl) is formed by reaction with sodium phosphate ($Na_3PO_4$)

(a-3) Reaction Formula:

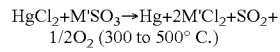

$$HgCl_2+M'SO_3 \rightarrow Hg+2M'Cl_2+SO_2+1/2O_2 \text{ (300 to 500° C.)}$$

wherein M' represents Ca or Mg. For example, more stable calcium chloride ($CaCl_2$) is formed by reaction with calcium sulfite ($CaSO_3$), and magnesium chloride ($MgCl_2$) is formed by reaction with magnesium sulfite ($MgSO_3$).

(a-4) Reaction Formula:

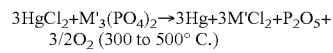

$$3HgCl_2+M'_3(PO_4)_2 \rightarrow 3Hg+3M'Cl_2+P_2O_5+3/2O_2 \text{ (300 to 500° C.)}$$

wherein M' represents Ca or Mg. For example, more stable calcium chloride ($CaCl_2$) is formed by reaction with calcium phosphate ($Ca_3(PO_4)_2$), and magnesium chloride ($MgCl_2$) is formed by reaction with magnesium phosphate ($Mg_3(PO_4)_2$).

(b) Acidic substances such as $SO_2$, $NO_2$, chlorine compound etc. are contained in a large mount in coal combustion exhaust gas, so when the reduction catalyst has a reduction action on $SO_2$, $NO_2$ etc., the function of reduction of $Hg^{2+}$ is substantially caused. In the catalyst such as inorganic carbonate, the reaction in which the basal part constituting the carbonate is replaced by a halide or nitrate proceeds gradually, and in use for a long time, the poisoning action of acidic substances on the catalyst is made significant and the reductive reaction characteristics are deteriorated.

(A-5) With Respect to an Indicator of the Reductive Reactivity of Salts

In view of the verification results described above, a specific indicator for judging whether salts have reductive reactivity or not can include ionic dissociation constant (pKa) (in an aqueous solution). Specifically, from the relationship with the acid dissociation constant of a typical compound shown in Table 2, the reductive reactivity of salts can be estimated to be high when pKa≦5, as shown in the thick frame of Table 2. For example, this corresponds to pK value of 2.15 of phosphate against that of 1.91 of sulfite, and it is also proven that from the results wherein $Na_3PO_4$ or $K_3PO_4$ attained 95% or more efficiency of reduction, as described above.

TABLE 2

|  |  | Acid Dissociation Constant(pKa) |
|---|---|---|
| Element as a Main Reagent | $H_2CO_3$ | 6.35 |
|  | HClO | 7.53 |
|  | HCN | 9.22 |
|  | $H_2CrO_4$ | 1.50 |
|  | HF | 3.17 |
|  | $H_2MoO_4$ | 3.62 |
|  | $H_3PO_4$ | 2.15 |
|  | $H_2SO_3$ | 1.91 |
|  | $H_2SeO_3$ | 2.75 |
|  | $H_2SiO_2$ | 9.93 |

(A-6) Catalyst Temperature and Reduction Efficiency

As described above, an Hg—Cl bond should be cleaved in order that the reagent of the present invention functions as a mercury reduction catalyst. That is, supply of dissociation energy for cleaving this bond, particularly energy not lower than the binding energy, are regarded as necessary. Theoretically, $Hg^{2+}$ is said to be thermally decomposed at 600° C. or more, thereby partially forming element mercury. The reaction is said to proceed stoichiometrically, but experimentally, the reaction rate is low, and for using the reagent in a mercury conversion unit by heat decomposition for pretreatment in an apparatus for measuring total mercury, use under a high-temperature condition at 850 to 900° C. is necessary. Accordingly, the efficiency of reduction of $HgCl_2$ was monitored with temperature as an indicator when the reagent of the present invention functions as the mercury reduction catalyst. As shown in FIG. 1, the result of verification using the reagents of the invention $K_2SO_3$ and $Na_2SO_3$ in the vicinity of $SV=1000\ hr^{-1}$ revealed 80% or more efficiency at 300° C. or more. With respect to $CaSO_3$, $MgSO_3$, $Na_3PO_4$ and $K_3PO_4$ or $Ca_3(PO_4)_2$ and $Mg_3(PO_4)_2$, the same results were confirmed at $SV=1000\ hr^1$. Under high-temperature conditions for more than 500° C., however, there arise secondary problems such as deterioration of sulfites, and thus the upper temperature in actual operation is preferably about 500° C. for maintaining the stability of sulfites. That is, it was found that a temperature of about 300 to 500° C. is preferable for a means of reductive reaction of a mercury compound such as $HgCl_2$ in the mercury conversion unit using the reagent of the present invention. The operative temperature of the catalyst is in the middle temperature range (300 to 500° C.) in which $Hg^{2+}$ can be selected reduced without reducing selenium oxide ($SeO_2$) and simultaneously the life of the catalyst can be significantly prolonged without undergoing the poisoning action of $SO_2$ gas etc.

(B) Unreactivity with Metal Oxides

Whereas reduction of a mercury compound into element mercury is essential for the apparatus for measuring total mercury in exhaust gas, as described above, metal oxides such as those of Pb and Se are contained in a relatively large amount in exhaust gas such as coal combustion exhaust gas, and thus in the process for reduction treatment of a mercury compound, reductive reaction with metal oxides simultaneously occurs to produce amalgam with mercury, thereby catching mercury to make accurate mercury measurement infeasible. That is, the mercury reduction catalyst is required to have unreactivity with such metal oxides, particularly a property of hardly forming amalgam with Pb, Se etc. The mercury reduction catalyst of the invention comprising the reagent of the invention as a main reagent could be proven to have very excellent unreactivity with metal oxides, as compared with that of the conventional catalyst. Particularly problematic $SeO_2$ was examined in a Hg reduction efficiency test in the coexistence of $HgCl_2$ and $SeO_2$.

(B-1) Test Method

The difference in the efficiency of reduction of $HgCl_2$ between the state where $SeO_2$ is absent and the state where $SeO_2$ is coexistent was verified. The catalyst temperature was 400° C., and the reagent of the invention, $K_2SO_3$, was used as the catalyst for reducing mercury. A standard gas previously examined for the concentration of $HgCl_2$ generated therefrom was prepared and introduced into the catalyst to confirm the efficiency of reduction of Hg. Then, predetermined amounts of $HgCl_2$ and $SeO_2$ were mixed to prepare a sample gas examined for the concentration of each gas generated therefrom (50 μg/m³ $HgCl_2$ as a standard with a varying concentration of $SeO_2$), and the sample gas was introduced into the catalyst in the coexistence of the two, and the influence of $SeO_2$ concentration on the efficiency of reduction of Hg was tested.

(B-2) Test Results

Figure 2:
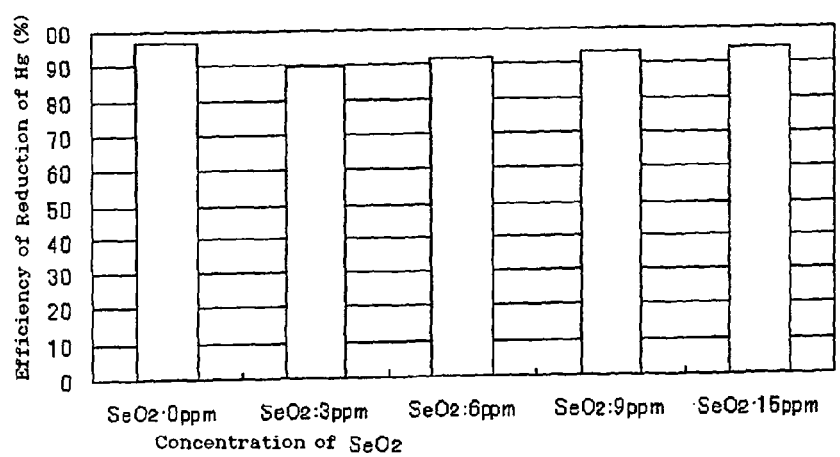
FIG. 2 is an illustration showing the influence of coexistent cesium oxide ($SeO_2$) on the efficiency of reduction of Hg.

The influence of $SeO_2$ concentration on the efficiency of reduction of Hg is also shown in FIG. 2. As compared with the efficiency of reduction of $HgCl_2$ without $SeO_2$, the efficiency in the coexistence of $SeO_2$ was not observed to be significantly lowered. It was found that even in the $SeO_2$ coexistent state, the function of reduction of $HgCl_2$ was not influenced.

(C) Poisoning Elimination Function of the Catalyst

Strongly acidic gases such as $SO_2$ contained in coal combustion exhaust gas can give a long-term poisoning action on the catalyst activity. On the other hand, the present inventors had found that "salts stable at high temperatures" such as phosphates and sulfites or basic substances forming sulfites can suppress such poisoning for a long time. That is, in the present invention, the reagent of the invention itself has such poisoning elimination function by which the high reducing function of the catalyst for reducing mercury can be maintained. Furthermore, the reagent of the invention is a chemically and physically stable compound even at 300 to 500° C. and is thus suitable as a catalyst for reducing mercury.

From the verification data shown above, it was found that a compound whose pKa is significantly deviated from 2, in the range of 300 to 500° C., easily causes the neutralization with strongly acidic gases such as $SO_2$ or is easily decomposed. That is, salts with pKa≦5 or pKa in the vicinity of 2 or less are suitable as catalyst substances effecting reductive reaction of $HgCl_2$ without undergoing the influence of strongly acidic gases contained in coal combustion exhaust gas, and are specifically substances represented by salts such as sulfites and phosphates.

Poisoning inhibitors against strongly acidic gases such as $SO_2$ are preferably those comprising phosphates or sulfites as a main reagent mixed with one or more basic substances forming sulfites. By using the reagent mixed with such two or more salts stable at high temperatures, the poisoning inhibiting effect on strongly acidic gases such as $NO_2$ or $Cl_2$ other than $SO_2$ coexistent in exhaust gas can be expected.

<Countermeasures for Suppressing Catalyst Crystallization>

The reagent of the present invention is based on a water-soluble compound such as sulfite and phosphate, and thus the presence of water in a sample can serve as water of crystallization to cause crystallization or recrystallization of the catalyst component. When crystallization occurs, the resistance of the catalyst layer to gas passage is increased, and the efficiency of reduction may be reduced. Against this, the present inventors found that the crystallization or recrystallization of the reagent comprising one component or similar salts easily occur, but hardly occurs where different salts are mixed. That is, as an agent inhibiting crystallization of the reagent of the invention, a basic salt that is a different kind of salt from the reagent of the present invention are mixed with the catalyst component, whereby recrystallization at high temperatures is prevented, a large reaction surface area can be maintained, and when a different kind of salt stable at high temperatures is partially mixed, recrystallization hardly occurs, and the effective area of the sulfite catalyst can be maintained for a long time. As the different kind of salt, basic salts such as Na salt and Ca salt are effective against K.

<Mercury Conversion Unit>

Figure 3:
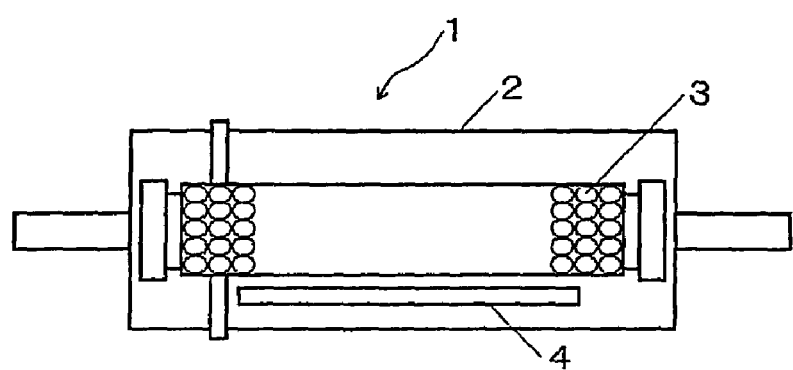
FIG. 3 is an illustration schematically showing the constitution of a mercury conversion unit.

The mercury reduction catalyst 3 prepared by the treatment described above is charged into a container 2 for using a mercury conversion unit 1 illustrated in FIG. 3, and is arranged in, for example, a sample treatment flow path of an apparatus for measuring total mercury in exhaust gas described later. The container 2 is composed of a strong, corrosion- and heat-resistant material. As the gas-contacting material, a material such as SUS causes reduced mercury to be easily oxidized, and thus inorganic materials such as glass, quartz and ceramics are preferable, and the metal is preferably oxidized SUS or Ti. When there is a large amount of dust etc. in exhaust gas, a dust-removing filter (not shown) can be arranged. The mercury conversion unit 1 is provided with a heating means 4 for adjusting the mercury reduction catalyst 3 to the optimum temperature to secure desired efficiency of reduction of mercury. When the mercury conversion unit is used in the apparatus for measuring total mercury in coal combustion exhaust gas, the reagent of the present invention is charged as the mercury reduction catalyst 3, and the operative temperature is maintained at 300 to 500° C.

Since the reagent of the present invention is originally powder, the reagent is compacted in the form of particles or granules. That is, the reagent is supported by a basic binder with an inorganic porous particle substance as a carrier for the catalyst and compacted in the form of particles or granules, thereby securing the surface area of the catalyst, preventing abrasion of the catalyst and maintaining high reducing function for a long time. In the following section, the method for this is described in detail.

<Method of Forming Granules or Particles of the Catalyst>

The reagent of the present invention is in a powdery form and is inherently easily crystallized by retaining crystal water as described above, so a method of impregnating a carrier with the reagent dissolved in an aqueous solution is not suitable in the conventional method of forming granules or particles. That is, in the present invention, refractory and/or activated alumina is used as the inorganic porous particle material, and a basic binder such as liquid glass and lithium silicate is used as the binder, whereby catalyst particles or granules easily handled as compact can be prepared while the surface activity of the reagent of the present invention is maintained.

(A) Method of Granulation of the Catalyst Substance 10 to 30% by weight of the reagent of the invention that is any of sulfites or a mixture thereof is impregnated into or adhered to an inorganic porous substance as a carrier.

(A-1) Selection of Inorganic Porous Substance

Such as Pamister (trade name: Ohe Chemicals inc.), activated alumina, activated carbon, and molecular sieve can be used as the carrier, and activated carbon and molecular sieve have catalyst performance themselves. These materials are selected on the basis of the characteristics of the reagent of the present invention and the binder. In the case of sulfite, for example, Pamister is preferable from the viewpoint of a larger amount of its adhering powder and higher retention.

(A-2) Method of Adhering to the Inorganic Porous Substance

Because any of the reagents of the present invention is water-soluble, water glass (chemical formula: $Na_2O.nSiO_2.xH_2O$), lithium silicate (chemical formula: $Li_2O.nSiO_2.xH_2O$) etc. are used as basic binders for preventing air oxidation by dissolution. As lithium silicate, there are types 35, 45 and 75 (manufactured by Nissan Chemical Industries, Ltd.).

(B) Operation of Granulation

Figure 4:
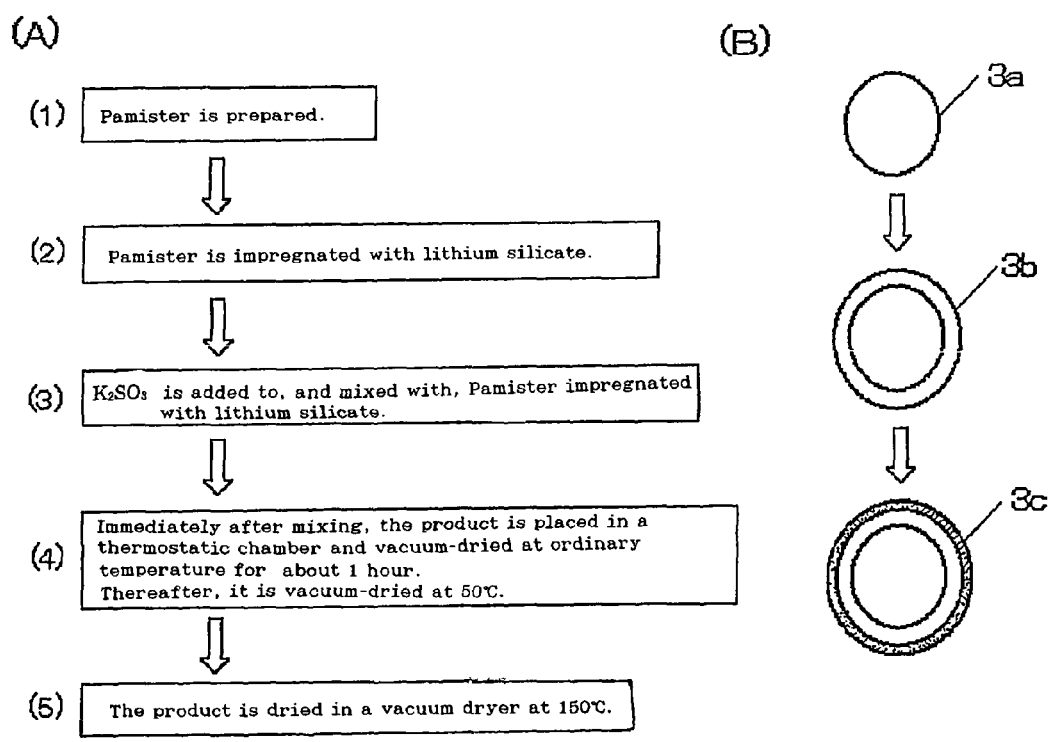
FIG. 4 is an illustration schematically showing a procedure of granulating a mercury reduction catalyst using sulfite.

For example, the operation, wherein $K_2SO_3$ as the reagent of the invention, lithium silicate as the binder, and Pamister as the carrier are used in granulation, is illustrated in FIG. 4(A), and the state of the particles is illustrated in FIG. 4(B). In this case, $K_2SO_3$ 3c is preferably adhered in a dry state, because when it is air-oxidized in a state dissolved in water, it becomes a sulfate and loses mercury reduction performance. Specific procedures for granulation are as follows:

(1) Pamister 3a is prepared. Pamister heat-treated at 600 to 800° C. for 6 hours or more in pretreatment is used.

(2) Pamister 3a is impregnated with lithium silicate. As shown in FIG. 4(B), a thin layer 3b of lithium silicate is formed on the surface of Pamister 3a.

(3) $K_2SO_3$ 3c is added to, and mixed with, Pamister 3a impregnated with lithium silicate. As shown in FIG. 4(B), $K_2SO_3$ 3c is adhered almost uniformly to the surface of the thin layer 3b of lithium silicate.

(4) Immediately after mixing, the product is placed in a thermostatic chamber and vacuum-dried at ordinary temperature for about 1 hour. Thereafter, it is vacuum-dried at 50° C.

(5) The product is dried in a vacuum dryer at 150° C. for 12 hours. As shown in FIG. 4(B), particles having $K_2SO_3$ 3c formed thereon are completed.

<Constitution of the Apparatus for Measuring Total Mercury in Exhaust Gas>

Figure 5:
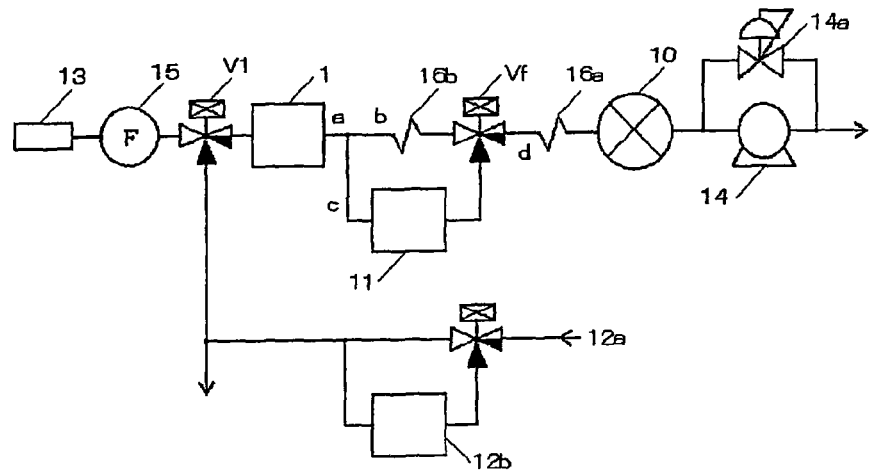
FIG. 5 is an illustration showing a constitution of an apparatus for measuring total mercury in exhaust gas.

FIG. 5 illustrates one constitution of the apparatus for measuring total mercury in exhaust gas by using the above catalyst for reducing mercury or the above mercury conversion unit 1. This constitution is suitable for the case where the subject of measurement is total mercury ($Hg^{2+}+Hg^0$) as a plurality of components containing the same element, such as divalent mercury ($Hg^{2+}$) and element mercury ($Hg^0$) which can be converted into each other. That is, $Hg^{2+}$ in the sample gas is first converted into $Hg^0$ as the object of measurement of the total amount of $Hg^0$, by the catalyst for reducing mercury or the mercury conversion unit 1, and by comparison with a gas obtained by selectively eliminating $Hg^0$, the influence of other existing components and the background can be eliminated. Hereinafter, the present invention is described by reference to the apparatus for measuring total mercury wherein the ultraviolet absorption analyzer 10 is used as a measurement means.

This constitution directed to $Hg^{2+}$ and $Hg^0$ as the object of measurement includes:

(1) as a sample treatment means, a mercury convention unit 1 for converting $Hg^{2+}$ selectively into $Hg^0$ and a purification apparatus 11 for selectively removing $Hg^0$ setting in one flow path c branched from a sample gas flow path a, (2) as a calibration means, a means of feeding $Hg^{2+}$-free and $Hg^0$-free zero gas and a means of feeding $Hg^0$ at predetermined concentration; and (3) as a measurement means, an ultraviolet absorption analyzer 10 for detecting the concentration of $Hg^0$ selectively, wherein in an arithmetic processing means (not shown), the detection function of $Hg^0$, calibration function and the treatment function of a sample treatment means are checked and treatment based on each function is carried out.

A sample is suctioned and collected through a sample inlet (corresponding to a sample collection means) 13 by a suction pump 14 arranged downstream of an ultraviolet absorption analyzer 10. The collected sample is cleaned with a dust filter 15 and then passes through valve V1 and then through a mercury conversion unit 1 arranged in flow path a and is divided into halves, while in (flow path c), $Hg^0$ in a sample is removed by the purification apparatus 11, and the sample is passed through a flow path resistance 16a and introduced into the ultraviolet absorption analyzer 10, whereas in (flow path b), the sample is not treated and passed through the flow path resistances 16b, 16a and introduced into the ultraviolet absorption analyzer 10. The flow path in which the absorption pump 14 was arranged is provided in parallel with a pressure regulating apparatus 14a, thereby forming a state which can be always suctioned from the upstream side, whereby loading on the suction pump 14 can be reduced and the suction pressure can be stably regulated. As the gas contacting material, metals such as Ti and oxidized SUS in addition to inexpensive glass, quartz and ceramics can be used.

Usually, at the time of usual measurement, flow paths b and c are switched periodically, and from a difference between the two, $Hg^{2+}$ is detected by an ultraviolet absorption analyzer 10. The switching between the two flow paths is carried out by an electromagnetic valve Vf arranged upstream of the ultraviolet absorption analyzer 10. At the time of zero calibration, zero gas is introduced via a calibration gas inlet 17a, passes through a flow path d and is introduced into the ultraviolet absorption analyzer 10. At the time of span calibration, span gas at a predetermined concentration generated from a generator 12b into which zero gas was introduced through calibration gas inlet 12a is introduced via flow path d into the ultraviolet absorption analyzer 10. Switching of valve Vf is carried out usually in a cycle of about 0.5 to 30 seconds. Measurement, calibration and checking are described detail below.

The ultraviolet absorption analyzer 10 (not shown) forms an optical system consisting of an ultraviolet light source part, a sample cell part, an ultraviolet detector and an optical filter, wherein the concentration of $Hg^0$ in the sample introduced into the sample cell part can be measured by detecting the amount of light (adsorbed by $Hg^0$ in the sample) in the ultraviolet region.

A purification apparatus 11 uses, for example, an adsorbent such as activated carbon, by which $Hg^0$ in the sample can be selectively adsorbed and removed. In addition, for example, Pt-silica- or Pd-alumina-based catalyst or a catalyst such as $V_2O$, is used to oxidize $Hg^0$ in a sample into $Hg^{2+}$ which cannot be detected with the ultraviolet absorption analyzer 10, whereby $Hg^0$ can be selectively removed. When an oxidization catalyst is used as the purification apparatus 11, the operative temperature can be the same middle-temperature range (for example 300 to 400° C.) as in the mercury conversion unit 1, and the two can be accommodated in the same unit to integrate of the temperature regulation mechanism and to downsize the apparatus.

Hg gas at predetermined concentration for calibration or verification cannot be prepared as high-pressure gas, and a generator 7 should be used. For example, zero gas is passed through a surface layer of Hg kept at predetermined temperature, or Hg permeating a permeation tube dipped in an Hg liquid bath is mixed with zero gas, whereby Hg gas at predetermined concentration can be obtained. By diluting it with zero gas, Hg gas at low concentration can be obtained.

Figure 6:
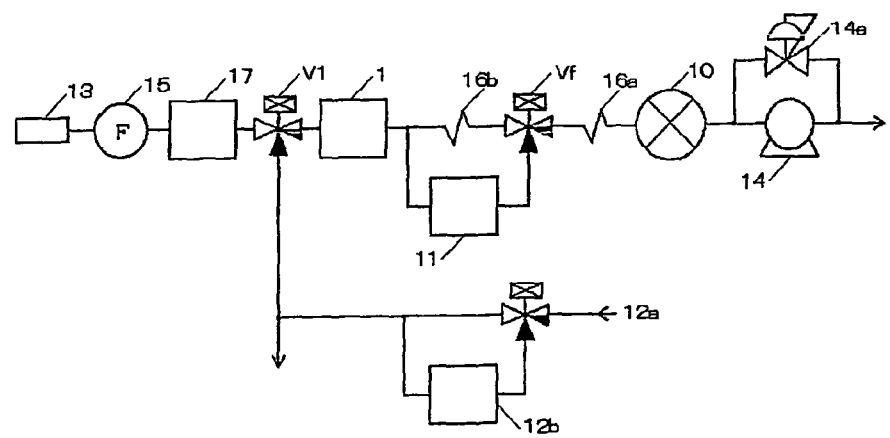
FIG. 6 is an illustration showing another constitution of an apparatus for measuring total mercury in exhaust gas.
Figure 7:
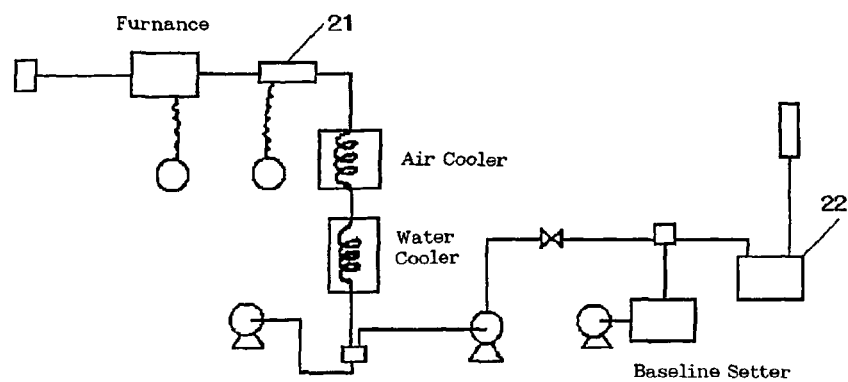
FIG. 7 is an illustration showing a constitution of a conventional method of continuously analyzing gaseous total mercury in exhaust gas.
Figure 8:
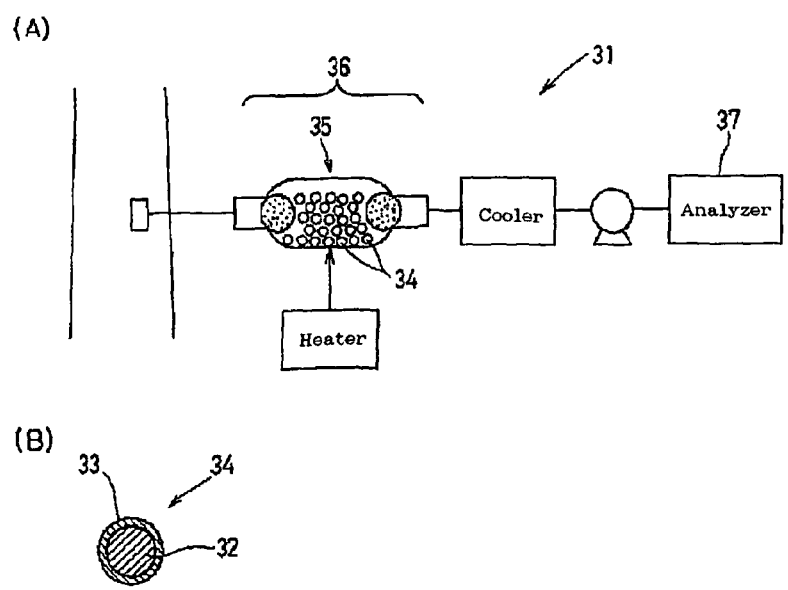
FIG. 8 is another illustration showing a constitution of a conventional method of continuously analyzing gaseous total mercury in exhaust gas.

FIG. 6 illustrates another constitution of the apparatus for measuring total mercury in exhaust gas, which uses the catalyst for reducing mercury or the mercury conversion unit 1 according to the present invention. The apparatus for measuring total mercury in exhaust gas comprises a scrubber unit 17 charged with a mist capturing agent or a counteragent arranged before a stage of the mercury conversion unit 1 in a sample collection path flow.

When substances such as $SO_3$ or oil mist causing corrosion of the sample collection flow path are contained in a large amount in a sample, such substances are removed with a scrubber unit 17, whereby the mercury reduction function of the mercury conversion unit 1 is maintained for a long time and is capable of continuous measurement with high accuracy and stability for a long time.

As the mist capturing agent, porous silica/alumina adsorbent is used whereby $SO_3$ mist, oil mist etc. in exhaust gas can be removed. Further, phosphoric acid has a function of improving a mist-capturing ability, and phosphoric acid is preferably adhered to the mist capturing agent. As a counteragent for strongly acidic gas, a basic substance forming a sulfite functioning as the reduction catalyst can be used to remove HCl or $Cl_2$ in exhaust gas. The concentration (content) of the counteragent can be increased to measure high-temperature exhaust gas containing a large amount of $SO_3$ mist. In this manner, one essential feature of the present invention lies in an excellent property of preventing poisoning action in addition to the catalyst function, which can be applied to the apparatus for measuring total mercury in exhaust gas, to bring about an excellent technical effect.

Measurement of total metal mercury in coal combustion exhaust gas, which has been difficult in the prior art, is made feasible highly accurately and highly sensitively with the apparatus for measuring total mercury in exhaust gas. In place of conventional batch measurement, completely continuous measurement can be realized. Particularly, the operative temperature of the catalyst for reducing mercury can be in the middle-temperature range (300 to 500° C.), whereby the reductive reaction of metal oxides in exhaust gas does not occur, and amalgam is not generated, and thus continuous measurement of mercury in exhaust gas is not hindered. As compared with the dilution method of using gold amalgam catching/concentrating operation that is the conventional standard measurement method, a diluting air source or a constant flow apparatus is not necessary, and the sampling system is simple, and the maintenance is easy.

In the foregoing, the present invention has been described mainly by reference to application to a catalyst for reducing mercury in coal combustion exhaust gas, a mercury conversion unit, and an apparatus for measuring total mercury, but can also be applied to samples similar in composition such as in process gas etc. or for study of various processes. The present invention is particularly useful when a sample in which $SO_2$ and metal oxides are coexistent is measured.

What is claimed is:

1. A catalyst for reducing mercury to enable a subsequent amalgam free form of the Hg to be released from the catalyst for measurement of the total mercury reduced by the catalyst, which comprises a reagent comprising any of the sulfites of potassium, sodium, calcium and magnesium, or any of the phosphates thereof, or a combination of them, as a main reagent of a catalyst component, wherein the catalyst reduces $Hg^{2+}$ into $Hg^0$ at a temperature of 300 to 500° C.

2. The catalyst for reducing mercury according to claim 1, wherein the catalyst component is mixed with a different salt as an agent for inhibiting crystallization of the catalyst component.

3. The catalyst for reducing mercury according to claim 2, wherein the catalyst component comprising the reagent as a main reagent is supported by a basic binder with an inorganic porous particle material as a carrier of the catalyst.

4. The catalyst for reducing mercury according to claim 3, wherein refractory and/or activated alumina is used as the inorganic porous particle material, and liquid glass and/or lithium silicate is used as the basic binder.

5. The catalyst for reducing mercury according to claim 1, wherein the catalyst component comprising the reagent as a main reagent is supported by a basic binder with an inorganic porous particle material as a carrier of the catalyst.

6. The catalyst for reducing mercury according to claim 5, wherein refractory and/or activated alumina is used as the inorganic porous particle material, and liquid glass and/or lithium silicate is used as the basic binder.

7. A catalyst for reducing mercury and releasing the reduced mercury for a measurement of the total amount of mercury comprising,
a main catalyst reagent consisting of a sulfite of one of potassium, sodium, calcium and magnesium or any of the phosphate thereof, and any combination thereof; and
a salt, of a different crystalline structure than the main catalyst reagent, of a sufficient amount to act as a crystallization inhibitor of crystallization of the main catalyst reagent, wherein the catalyst reduces $Hg^{2+}$ into $Hg^0$ at a temperature of 300 to 500° C.

8. The catalyst of claim 7 wherein the main catalyst reagent is $Na_2SO_3$ and the salt is selected from a group consisting of $CaCO_3$, $CaSO_4$ and $BaCO_3$.

9. The catalyst of claim 7 further including an inorganic porous particle material for supporting the main catalyst reagent with a binder material.

10. The catalyst of claim 9 wherein the inorganic porous particle material is a refractory and/or activated alumina.

11. The catalyst of claim 10 wherein the binder material is one of liquid glass and lithium silicate and the main catalyst reagent is formed into one of a particle and honeycomb shape.

12. A catalyst for reducing mercury from a combustion exhaust gas to enable measurement of the total mercury content in the combustion exhaust gas, at a temperature in the range of 300° C. to 500° C., consisting of:
a main catalyst reagent consisting of a sulfite of one of potassium, sodium, calcium and magnesium or any of the phosphate thereof, and any combination thereof;
a salt, having a different crystalline structure than the main catalyst reagent, of a sufficient amount to act as a crystallization inhibitor of crystallization of the main catalyst reagent, wherein the catalyst reagent reduces $Hg^{2+}$ into $Hg^0$, without a reduction reaction with metal oxides, to continuously release $Hg^0$ from the main catalyst reagent measurement; and
an inorganic porous particle material and binder material operatively supporting the combination of the main catalyst reagent and the salt crystallization inhibitor in a configuration to release the $Hg^0$ after the reduction reaction of the combustion gas by the catalyst reagent for subsequent measurement of the total amount of mercury.

13. The catalyst of claim 12 wherein the main catalyst reagent is $Na_2SO_3$ and the salt is selected from a group consisting of $CaCO_3$, $CaSO_4$ and $BaCO_3$.

14. The catalyst of claim 13 wherein the inorganic porous particle material is one of a refractory and/or activated alumina.

15. The catalyst of claim 14 wherein the binder material is one of liquid glass and lithium silicate and the main catalyst reagent is formed into a honeycomb shape.

16. The catalyst of claim 14 wherein the binder material is one of liquid glass and lithium silicate and the main catalyst reagent is formed into a particulate shape.

17. A catalyst for reducing mercury from a combustion exhaust gas to enable measurement of the total mercury content in the combustion exhaust gas, at a temperature in the range of 300° C. to 500° C., comprising:
a main catalyst reagent consisting of $Na_2SO_3$;
a salt, selected from a group consisting of $CaCO_3$, $CaSO_4$ and $BaCO_3$, having a different crystalline structure than the main catalyst reagent, and of a sufficient amount to act as a crystallization inhibitor of crystallization of the main catalyst reagent, wherein the catalyst reagent reduces $Hg^{2+}$ into $Hg^0$, without a reduction reaction with lead and/or selenium in the exhaust gas to continuously release an amalgam free form of $Hg^0$ from the main catalyst reagent measurement; and
an inorganic porous particle material and binder material operatively supports the combination of the main catalyst reagent and the salt crystallization inhibitor in a configuration to release the amalgam free $Hg^0$ after the reduction reaction of the combustion gas by the catalyst reagent for subsequent measurement of the total amount of mercury.

18. The catalyst of claim 17 wherein the main catalyst reagent is $Na_2SO_3$ and the salt is selected from a group consisting of $CaCO_3$, $CaSO_4$ and $BaCO_3$.

19. The catalyst of claim 18 wherein the inorganic porous particle material is one of a refractory and/or activated alumina.

20. The catalyst of claim 19 wherein the binder material is one of liquid glass and lithium silicate and the main catalyst reagent is formed into a honeycomb shape.

* * * * *